United States Patent [19]

Nazar

[11] Patent Number: 5,567,867
[45] Date of Patent: Oct. 22, 1996

[54] DROP WEIGHT TYPE IMPACT TESTING MACHINE

[76] Inventor: Ladislao M. Nazar, 9511 Florimond Road, Richmond, British Columbia, Canada, V7E 1M2

[21] Appl. No.: 511,437

[22] Filed: Aug. 4, 1995

[51] Int. Cl.⁶ .................................................. G01M 7/00
[52] U.S. Cl. ........................ 73/12.13; 73/12.06; 173/90
[58] Field of Search .............................. 73/12.01, 12.04, 73/12.06, 12.07, 12.09, 12.11–12.14; 173/210, 211, 212, 90, 92, 118, 117, 122, 124

[56] References Cited

U.S. PATENT DOCUMENTS

| | | | |
|---|---|---|---|
| 3,106,834 | 10/1963 | Parstorfer | 73/12.06 |
| 3,209,580 | 10/1965 | Colby | 73/12.06 |
| 3,402,593 | 9/1968 | Bresk et al. | 73/12.07 |
| 3,485,083 | 12/1969 | Gray et al. | 73/12.06 |

OTHER PUBLICATIONS

Satec Corporation, Drop–Weight Testers, undated.
General Research Corp., Dynatup GRC 8200, undated.

Primary Examiner—Robert Raevis
Attorney, Agent, or Firm—Norman M. Cameron

[57] ABSTRACT

An impact testing apparatus includes a main frame mounted on a main frame base. There is a pair of spaced-apart guide columns with an impact hammer slidably mounted thereon. A lifting beam is slidably mounted on the guide columns above the impact hammer and can be raised by a hoist to the top of the main frame. There is a specimen base adjacent the main frame base. There is a movable joint between the specimen base and the main frame base, whereby the main frame base is isolated from shock resulting from impact of the hammer on the specimen base. Preferably the joint is occupied by a non-rigid member, such as an elastomeric member. Preferably there is adjustable means for tensioning the guide columns. There may be an electromagnetic latch between the lifting beam and the impact hammer.

4 Claims, 6 Drawing Sheets

FIG. 8
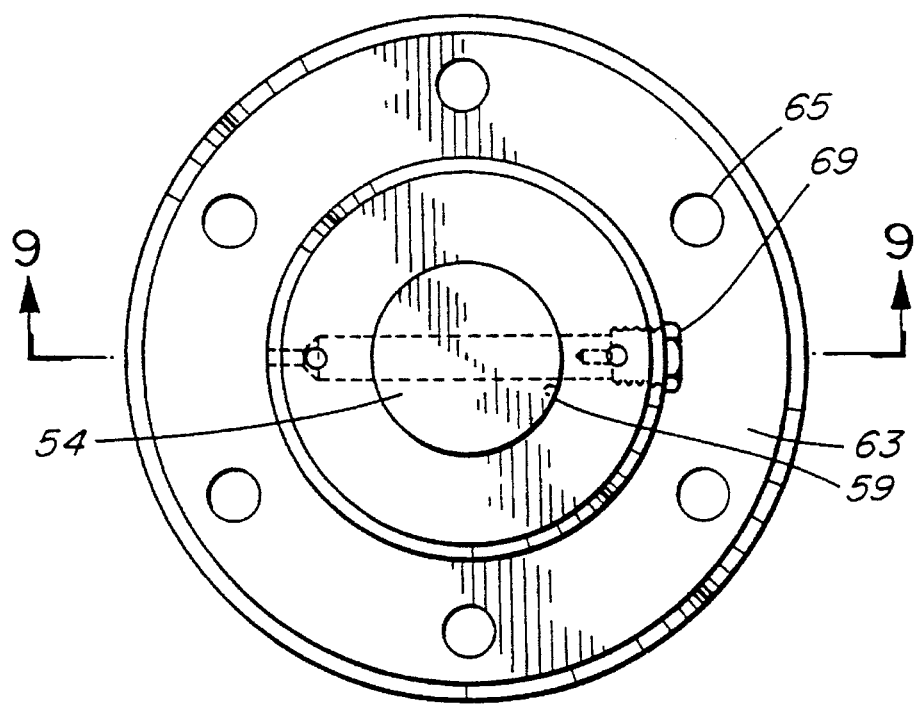
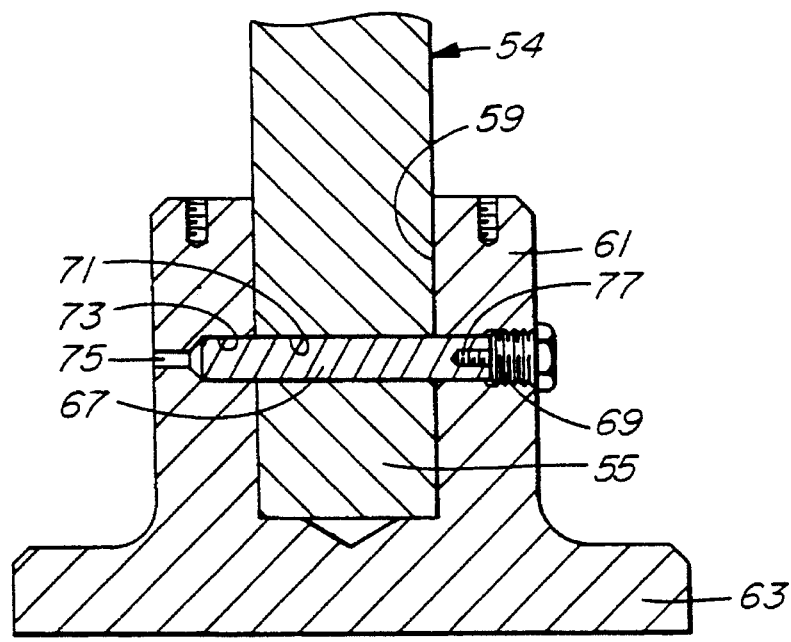
FIG. 9

DROP WEIGHT TYPE IMPACT TESTING MACHINE

BACKGROUND OF THE INVENTION

This invention relates to drop weight type impact testing machines.

Many machines have been developed in the past for testing materials. One approach has been to try and reproduce the type of failure which may occur to ensure that the materials being tested can withstand the forces and conditions they will encounter in use.

Recent earthquakes, both in California and Japan, have led to doubts about the reliability of testing apparatuses and procedures in place prior to those events. Failure of various structures occurred despite the fact that they were deemed to be "earthquake proof". One example is concrete structures, such as concrete columns and beams used on elevated freeways. Catastrophic collapse of these structures, with considerable loss of life and significant property damage, occurred despite the fact that some of the collapsed structures theoretically should have been capable of withstanding the forces of the earthquakes involved.

This has led to a demand for improved testing machines and procedures, particularly for concrete and reinforced concrete structures. There is a need to test relatively large concrete members for impact resistance. Many apparatuses have been designed in the past for impact testing, but are not suitable for testing such large concrete members with the high impact forces necessary. The amount of force involved in testing large concrete members can easily destroy a testing machine or even damage the foundation and building containing the machine.

Accordingly it is an object of the invention to provide an improved impact testing apparatus which overcomes disadvantages associated with earlier devices of the general type.

It is also an object of the invention to provide an improved impact testing apparatus which can withstand the high impact forces involved in impacting relatively large members of concrete or other materials without damage to the apparatus itself, its foundations or buildings housing it.

It is a further object of the invention to provide an improved impact testing apparatus utilizing a heavy impact hammer which can be raised above a specimen and easily released in order to be dropped on the specimen.

It is a still further object of the invention to provide an improved impact testing apparatus with a sliding impact hammer which can drop freely without binding.

SUMMARY OF THE INVENTION

In accordance with these objects there is provided a drop weight type impact testing apparatus including a main frame mounted on a main frame base. There is an impact hammer and a hoist mounted on the frame and engagable with the impact hammer for lifting the hammer. There is a specimen base adjacent the main frame base having means for mounting a specimen thereon. There is a movable joint between the specimen base and the main frame base, whereby the main frame base is isolated from shock resulting from impact of the hammer on a specimen mounted on the specimen base.

For example, the main frame base may be annular with a central opening. The specimen base is located in the central opening of the main frame base. There may be a non-rigid member, such as an elastomeric member, between the specimen base and the main frame base.

There may be spaced-apart vertical guide columns mounted on the frame. The hammer is slidably mounted on the columns. There may be means for tensioning the guide columns.

There may be a lifting beam guidably mounted on the guide columns above the impact hammer. An electromagnetic latch On the lifting beam can selectively engage the hammer to raise the hammer.

The invention offers significant advantages compared with many prior art impact testing apparatuses. The invention is capable of providing an apparatus for impact testing large specimens, such as concrete beams,i and handling the large shock forces involved without damage to the apparatus, its foundations or buildings containing it. Furthermore, the invention provides an apparatus wish an impact hammer which can be easily raised and dropped on a specimen without binding, despite having a relatively large weight.

BRIEF DESCRIPTION OF THE DRAWINGS

In the drawings:

FIG. 8 is a top plan view of a column foot support housing; and

FIG. 9 is a sectional view taken along line 9—9 of FIG. 8.

DESCRIPTION OF THE PREFERRED EMBODIMENTS

Figure 1:
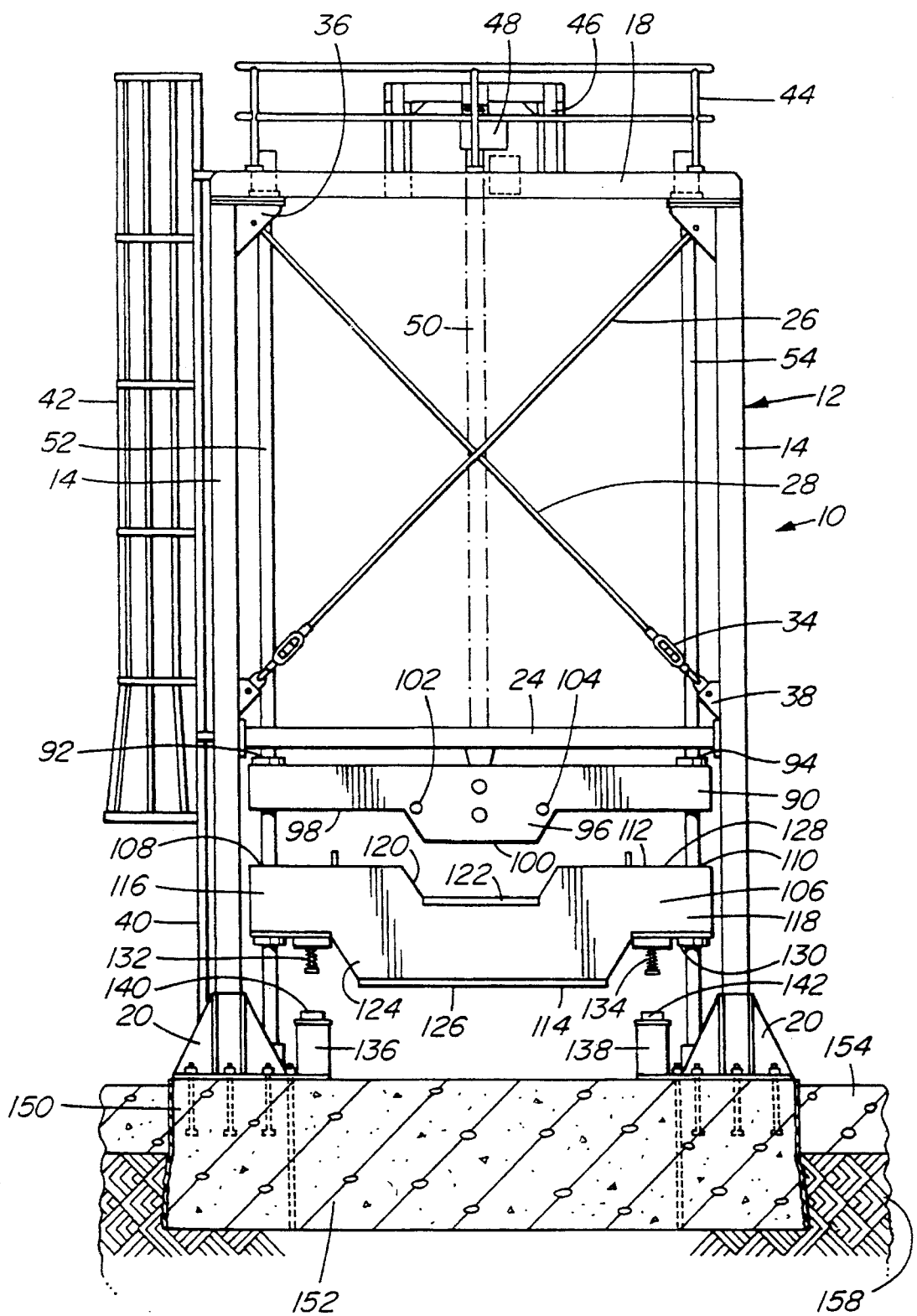
FIG. 1 is a front elevation of an impact testing apparatus according to an embodiment of the invention and the bases thereof.
Figure 2:
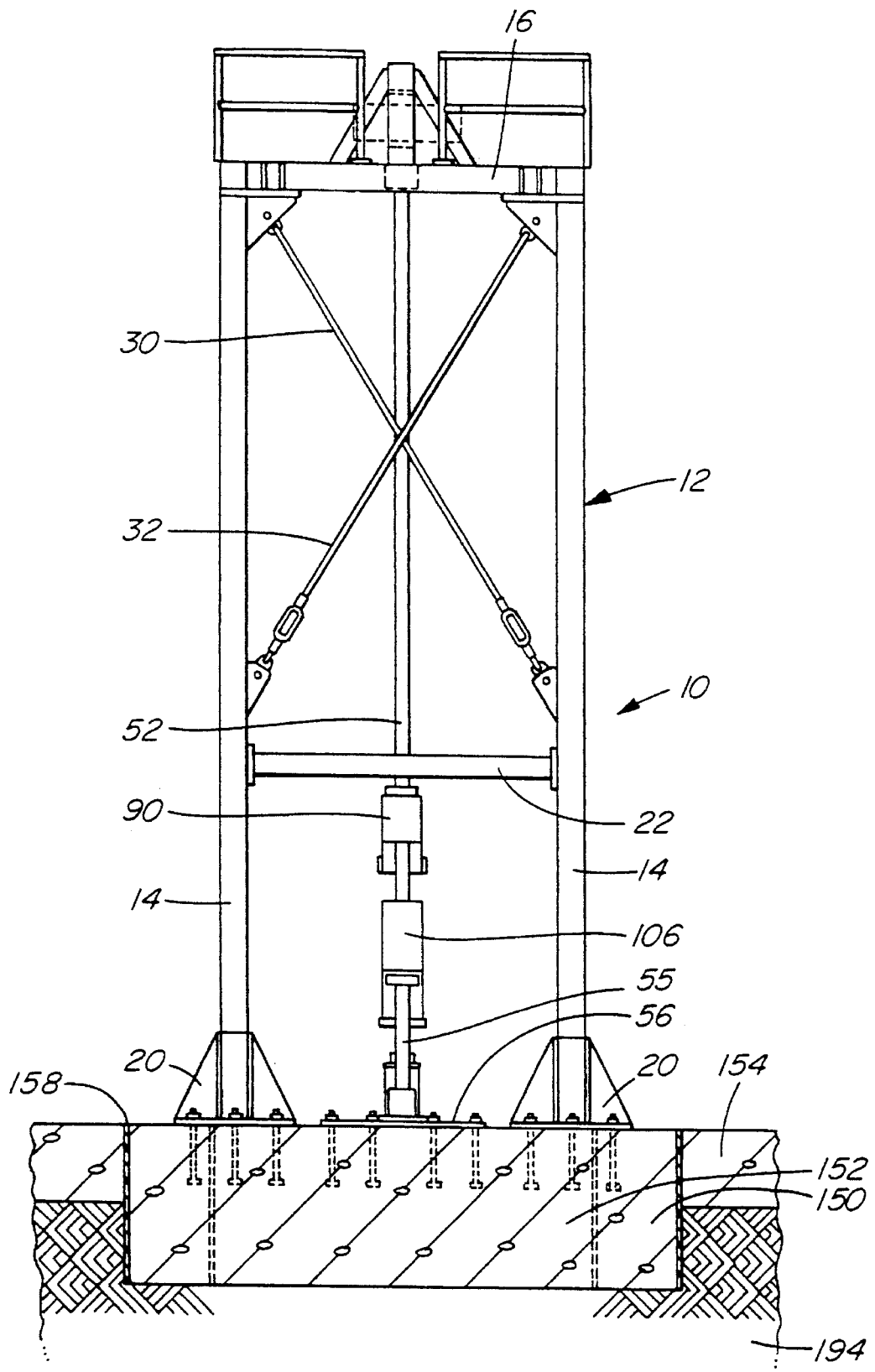
FIG. 2 is a side view thereof.

Referring to the drawings, and first to FIG. 1 and 2, these show a drop weight type impact testing machine or apparatus 10 which is relatively large in size and is intended for impact testing of large objects such as concrete beams. The particular example shown is approximately 27 feet high although other examples may be larger or smaller depending upon requirements. The structure is generally of steel, apart from the bases. The apparatus includes a main frame 12 having four vertical supports 14 arranged at corners of a rectangle. The supports 14 are connected at the tops thereof by four horizontal members including a pair of shorter members 16 and a pair of longer members 18. The vertical supports have base plates 20 at the bottoms thereof. There are also four horizontal braces connecting the vertical supports above their bottoms including shorter braces 22 and longer braces 24.

There is also a pair of cross braces on each side of the frame including braces 26 and 28 on the front and on the back of the frame and braces 30 and 32 on each end. The cross braces are rods with turnbuckles 34 provided tier tensioning thereof. As seen for cross brace 28, each is connected to a gusset plate 36 at the top at one top corner of the frame and to a bracket 38 at the bottom.

The frame 12 is provided with a ladder 40 on one end including a safety guard 42 and a catwalk 44 on the top thereof although these features are optional.

There is also a hoist frame 46 mounted on top of the main frame for supporting a hoist 48. The hoist is capable of winding Dr unwinding chains 50 which extend downwardly therefrom. In this particular embodiment a Coffing 5 Ton hoist, Model EC 10008-3 is used but other hoists or hoisting means could be substituted. The chain bucket may be modified to reduce vertical clearance by making it shorter in height but longer, with a sloped bottom so the chain tends to move to one end thereof.

There is a pair of guide columns 52 and 54 mounted vertically in the frame. Each column has a bottom 55, as shown for column 54 in FIG. 9, which fits within socket 59 of a column foot support housing 61. Each housing has a bottom flange 63, with a plurality of spaced-apart bolt holes 65, shown in FIG. 8, for mounting the housing on specimen base 166 described below. A pin 67, held in place by a short bolt 69, fits tightly in bore 71 in the column and bore 73 on each side of the housing. The bolt is at one end of bore 73 in a threaded portion thereof. There is a small bore 75 at the opposite end of the bore 73 for inserting a smaller pin to drive out pin 67 when required. There is a threaded aperture 77 on pin 67 adjacent the bolt 69 to permit a puller to be secured to pin 67 after the bolt is removed, to aid in removing the pin.

In this embodiment the guide columns are chromed, precision ground solid shafting which is machined to close tolerances.

Figure 3:
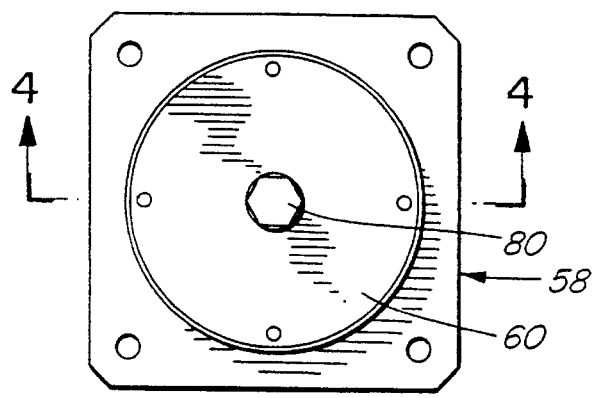
FIG. 3 is a top view of the tension adjusting device for one of the columns thereof.
Figure 4:
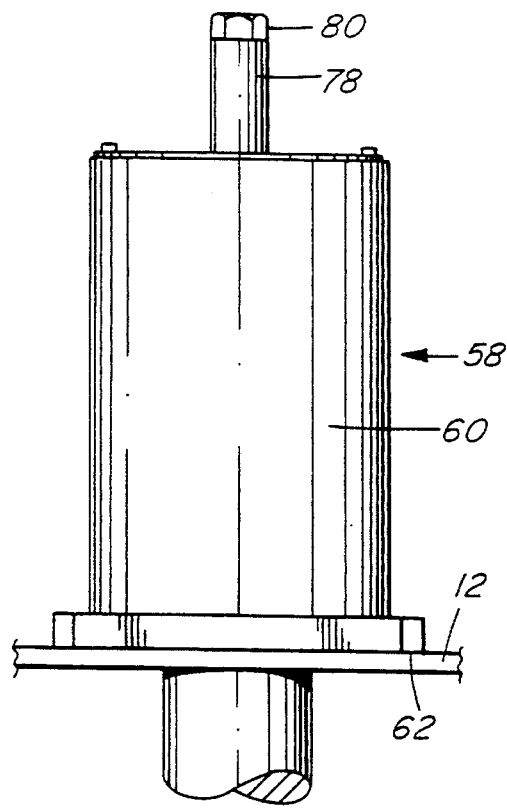
FIG. 4 is a side elevation thereof.
Figure 4A:
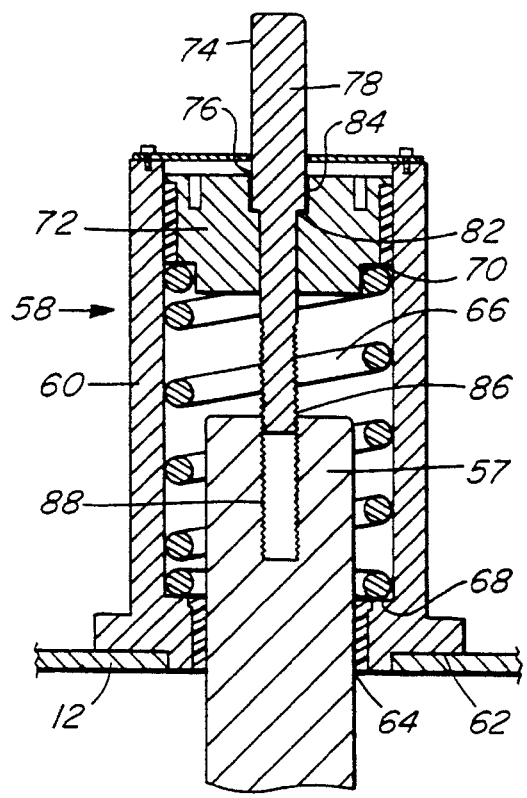
FIG. 4a is a sectional view taken along line 4—4 of FIG. 3.

Each guide column has a top 57 provided in this example with a tension adjusting device 58 shown best in FIG. 3, 4 and 4a. Each device includes a hollow, cylindrical housing 60 with a bottom 62 mounted on the main frame 12. There is a circular opening 64 at the bottom of each housing which slidably receives the top 57 of the column.

There is a coil spring 66 compressed within the housing between an internal shoulder 68 on the bottom thereof and annular groove 70 on a movable support 72.

There is a rotatable bolt or member 74 extending rotatably through aperture 76 in the support 72. There is a sleeve 78 extending about the bolt below its head 80 and supported at the bottom by annular shoulder 82 at the bottom of larger diameter portion 84 of the aperture 76. Bolt 74 has a threaded portion adjacent the bottom 86 thereof which threadedly engages female threaded aperture 88 extending downwardly from top 57 of the guide column. Thus it may be seen that the tension in the column can be adjusted by turning bolt 74 by means of head 80 to pull the guide column a greater or lesser amount and thereby tension spring 66 a corresponding greater or lesser amount.

Figure 7:
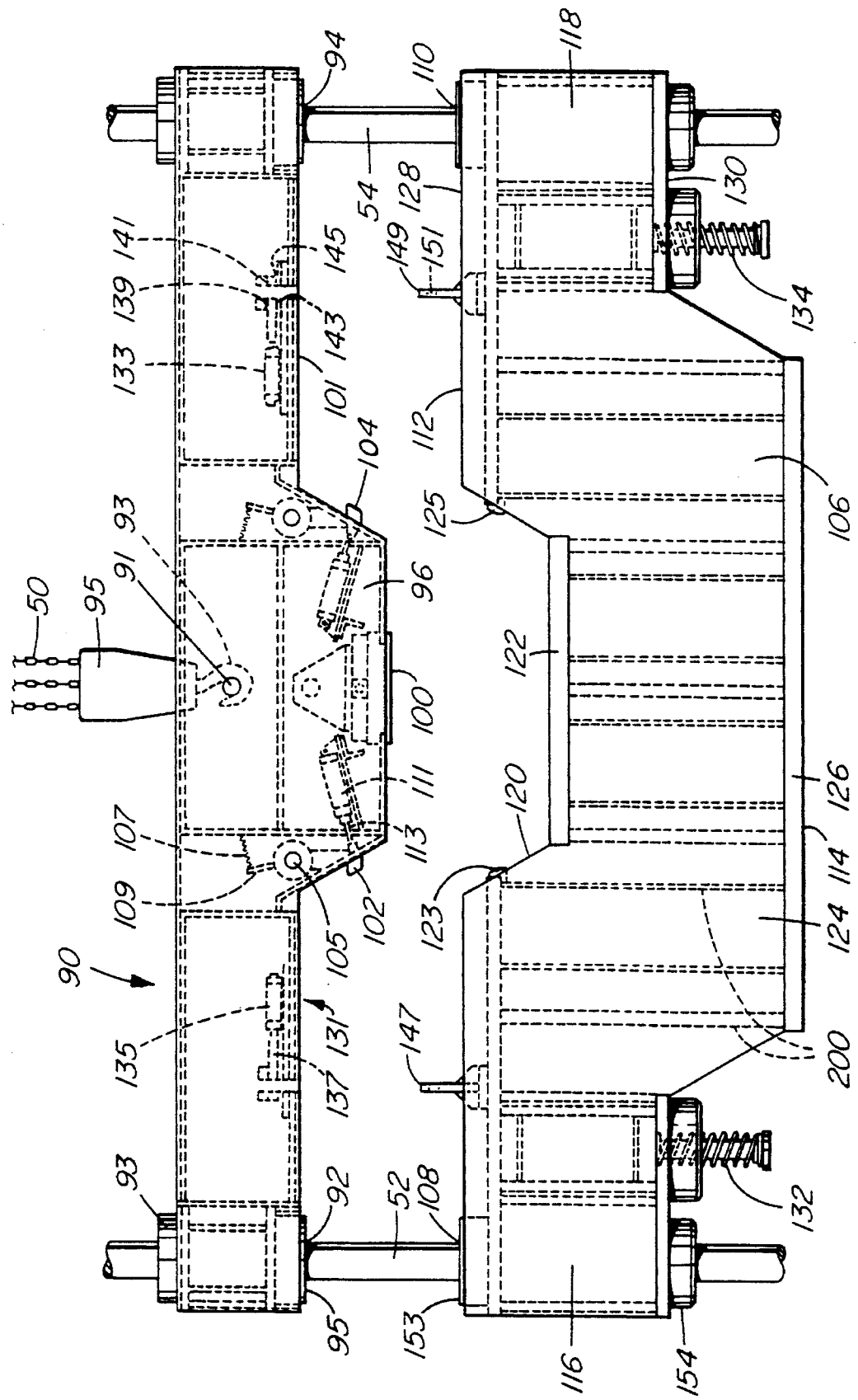
FIG. 7 is a front elevation of the lifting beam and impact hammer beam of FIG. 1, with internal components in stippled lines.

There is a lifting beam 90 extending horizontally between the guide columns as shown best in FIG. 7. The lifting beam has two cylindrical apertures 92 and 94, each equipped with suitable bushings 93 and 95, at each end thereof for guidably receiving the guide columns 52 and 54. These permit the lifting beam to be raised or lowered along the guide columns by means of the chains 50 and hoist 48. There is a pin 91 at the center of beam 90 used to connect hook 93 on the end of block 95 suspended from chains 50.

The lifting beam has a trapezoidal projection 96 on bottom 101 thereof equipped with an electromagnet 100.

There are also safety catches 102 and 104 adjacent each side of the projection. Each safety catch is pivotally mounted on a pin 105. The catches are biased outwardly by a coil spring 107 connected to arm 109 on the catch in this example. There is a reverse acting air cylinder 111 having a rod 113 connected to each catch. Such cylinders have internal springs so as to normally bias the latches outwardly. The cylinders have pistons which retract the latches when pressurized air is supplied to the cylinders.

Lifting beam 90 is used to raise impact hammer beam (also referred to as "impact hammer") 106 to a raised position near the top of main frame 12. The impact hammer beam is provided with a pair of cylindrical apertures 108 and 110, provided with bushings 153 and 154 similar to the apertures 92 and 94 in the lift beam, which guidably receive the guide columns 52 and 54. The impact hammer beam has atop 112 and a bottom 114. It has end portions 116 and 118 adjacent the apertures 108 and 110.

There is a trapezoidal-shaped recess 120 in the top thereon which is complementary in shape to the projection 96 on the lifting beam. There is a horizontal plate 122 in the recess of a magnetic material which releasably engages the electromagnet 100. A pair of latches 123 and 125 are provided on opposite sides of the recess which automatically engage latches 102 and 104 of the lifting beam when the lifting beam is lowered onto the hammer.

The lifting beam also has a pair of safety latches 131 and 133. Each includes a pneumatic cylinder 135 connected to a pin 137 slidably receivable in apertures 139 and 141 of spaced-apart lugs 143 and 145. The impact hammer beam has a pair of lugs 147 and 149, each provided with an aperture 151. The lugs 147 and 149 fit between lugs 139 and 141 when the lifting beam lowered onto the impact hammer beam and pins 137 of the cylinders 135 can be deployed through all three lugs to prevent the impact hammer beam from accidentally dropping. Neither the automatic safety catches 102 and 104, nor the latches 131 and 133 normally carry the weight of the raised impact hammer. This is accomplished by the electromagnet. The catches act as dual safety devices in the event of power failure.

The impact hammer beam has a trapezoidal projection 124 adjacent the bottom thereof provided with a heavy plate 126 intended to impact the Specimen. The impact hammer beam is generally box-like with vertical internal supports 200. The configuration of the beam, including the projection 124 on the bottom with the heavy plate 126, means that its center of gravity is below the magnet and between the tops 128 and bottoms 130 of end portions 116 and 118 of the beam. This relatively low center of gravity ensures that the impact hammer beam can drop freely without binding on the guide columns.

There are a pair of hydraulic decelerators 132 and 134 mounted on the bottoms 130 of the end portions 116 and 118 inwardly from the guide columns 52 and 54. These hydraulic decelerators are well known and are intended to absorb any remaining momentum of the impact hammer beam after it has impacted a specimen. The decelerators used in this example originate with Ace Controls Inc. as model CA4XS-FRP-1, though others could be substituted.

There is a pair of pneumatic jacks 136 and 138 mounted at positions below the decelerators 132 and 134 as seen in FIG. 1. The jacks have contact members or stops 140 and 142 which can be raised when the jacks are actuated with air pressure. In their lowered positions, as shown in FIG. 1, the jacks serve as contact points for the hydraulic decelerators.

Figure 5:
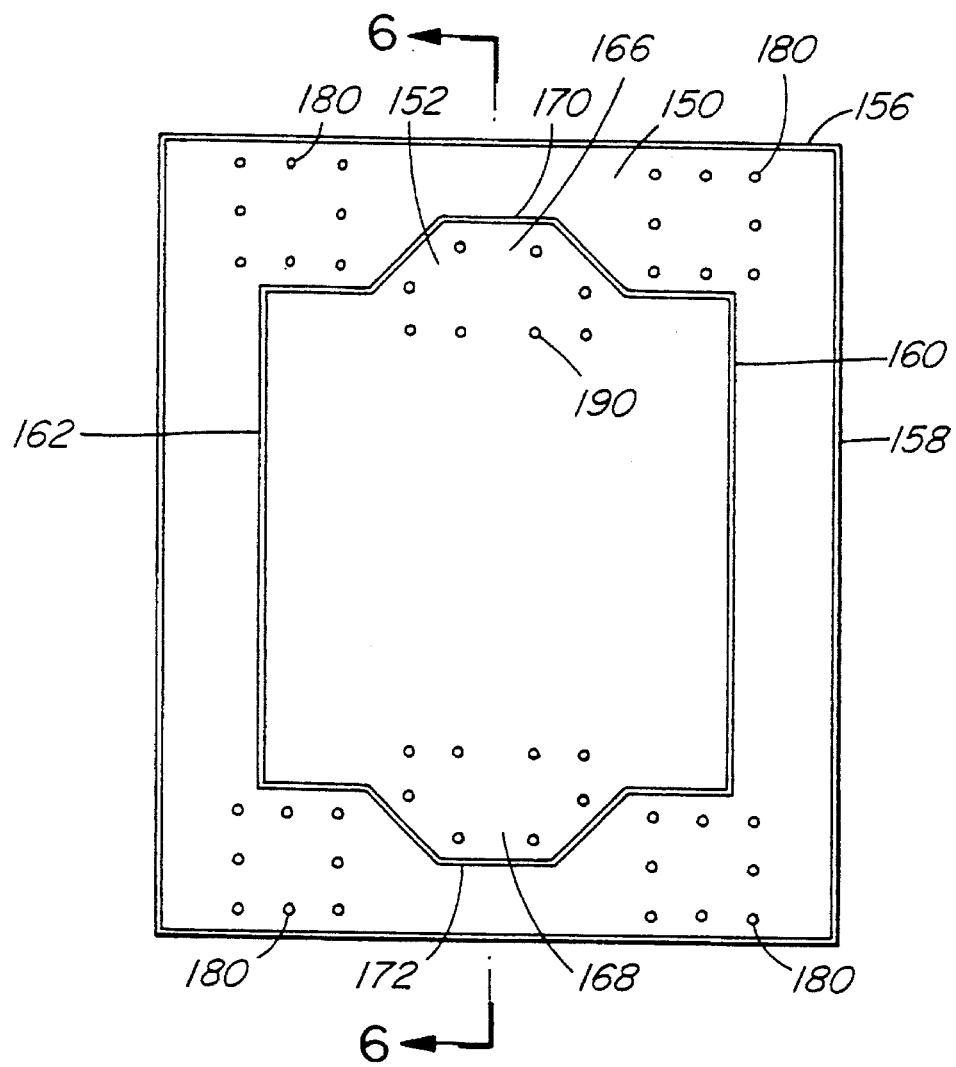
FIG. 5 is a top plan view of the bases thereof.
Figure 6:
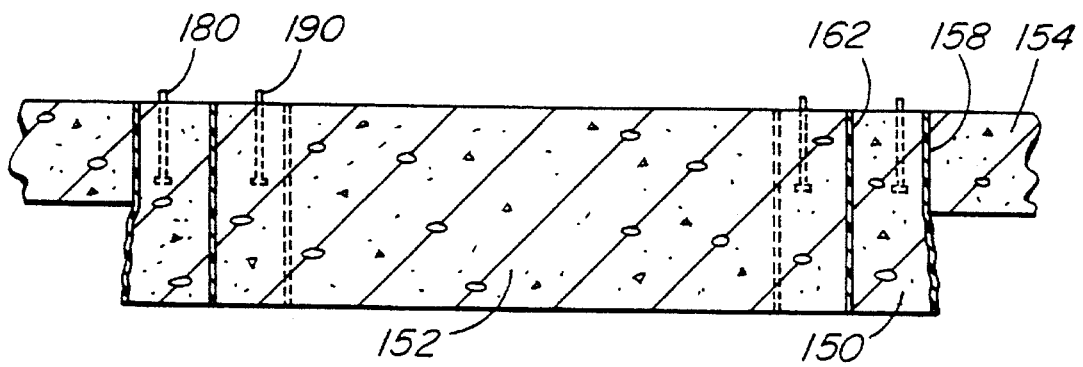
FIG. 6 is a sectional view taken along line 6—6 of FIG. 5.

The apparatus includes two separate bases or foundations including a main frame base 150 and a specimen base 152 which are best shown in FIG. 5 and also in FIG. 1, 2 and 6. It may be seen that the main frame base in plan is annular and rectangular in shape. As shown best in FIG. 1 and 2, it is separate from floor or foundation 154 of the building or work area where the apparatus is located. There is a four sided joint 156, rectangular in plan, extending between the main frame base and the foundation or floor 154. In this particular example there is a non-rigid member 158 between the exterior of the main frame base 150 and the floor or foundation 154. In this particular example the member is of rubber or a similar synthetic elastomeric material.

There is a similar joint 160 between the inside of the main frame base and specimen base 152, also provided with a similar non-rigid member 162.

It may be seen best in FIG. 5 that the specimen base 152 has trapezoidal projections 166 and 168 on each side thereof which fit into corresponding trapezoidal recesses 170 and 172 in the main frame base. The non-rigid member 162 and the joint 160 extend between the trapezoidal projections and the corresponding recesses. The top surface of the specimen base in this example provides means for mounting a specimen on the base. Alternatively spaced-apart beams or the like can be placed over the base to support the specimen.

There are four sets of bolts 180 near the four corners of the main frame base used to connect the main frame base plates 20 to the base 150. Similarly the specimen base has bolts 190 on opposite sides thereof used to mount the pneumatic jacks 136 and 138 as well as the bottoms of the guide columns.

In this example the two bases 150 and 152 as well as the foundation or floor 154 are made of reinforced concrete although other materials could be substituted. All three are located on compressed sand although again other alternative materials could be used.

Operation

The central area of the specimen base 152 between the bolts 190 is utilized as a means for supporting specimens to be impacted. The impact hammer beam is raised by first lowering the lifting beam 90 until the electromagnet 100 contacts plate 122 on the impact hammer beam. The electromagnet is then energized. Hoist 48 and chain 50 are then used to raise the lifting beam and consequently the impact hammer beam to the top of frame 12 or some intermediate point between the top and the bottom depending upon the impact force desired. When the desired height is reached, the hoist is stopped. During the lifting operation safety catches 102 and 104 as well as latches 131 and 133 prevent the impact hammer beam from dropping in the event that power to the electromagnet is lost. However the weight of the beam is normally carried by the electromagnet and not by the safety latches or catches. After the specimen is in position on the specimen base, the impact hammer beam can be dropped by cutting off electrical power to the electromagnet 100. This causes the impact hammer to drop along the guide columns 52 and 54 until plate 126 contacts the specimen. Any additional downward momentum of the impact hammer beam is absorbed when the decelerators 132 and 134 hit contact members 140 and 142 on pneumatic jacks 136 and 138.

After the specimen has been impacted, it is desirable to raise the impact hammer beam in order to examine the specimen. This is done by providing compressed air to the jacks 136 and 138 which raise the impact hammer beam a distance above the specimen. This can be done automatically using a sensor, such as a photo cell, which senses the arrival of the impact hammer beam.

It will be understood by someone skilled in the art that many of the details described above are by way of example only and are not intended to limit the scope of the invention which is to be interpreted with reference to the following claims.

What is claimed is:

1. An impact testing apparatus, comprising:

a main frame;

spaced-apart vertical guide columns mounted on the main frame;

an impact hammer beam slidably mounted on the guide columns;

a hoist near the top of the main frame;

a lifting beam guidably mounted on the guide columns above the impact hammer beam and operatively connectable to the hoist, one said beam being selectively engageable with a second said beam, whereby the lifting beam can raise the impact hammer beam; and a safety catch releasably interconnecting the beams and an actuator operatively connected to the catch.

2. An apparatus as claimed in claim 1, including means for biasing the catch into a position which interconnects the beams.

3. An apparatus as claimed in claim 2 having a pair of said catches and said actuators, each said actuator being a reverse acting fluid cylinder and the means for biasing being an internal spring thereof.

4. An apparatus as claimed in claim 3, wherein there is also a pair of safety latches releasably interconnecting the beams, each said latch including lugs on the beams having apertures, a pin slidably engagable with the apertures in the lugs and fluid cylinder operatively connected to the pin.

* * * * *